(12) United States Patent
Neev

(10) Patent No.: US 12,115,297 B2
(45) Date of Patent: Oct. 15, 2024

(54) SYSTEM AND METHOD FOR DAMAGING VIRUSES

(71) Applicant: LASER VIRAL TECHNOLOGIES (LVT) LTD., Raanana (IL)

(72) Inventor: Joseph Neev, Laguna Beach, CA (US)

(*) Notice: Subject to any disclaimer, the term of this patent is extended or adjusted under 35 U.S.C. 154(b) by 0 days.

(21) Appl. No.: 17/915,550

(22) PCT Filed: Mar. 29, 2021

(86) PCT No.: PCT/IL2021/050356
§ 371 (c)(1),
(2) Date: Sep. 29, 2022

(87) PCT Pub. No.: WO2021/199038
PCT Pub. Date: Oct. 7, 2021

(65) Prior Publication Data
US 2023/0133333 A1    May 4, 2023

Related U.S. Application Data

(60) Provisional application No. 63/075,125, filed on Sep. 5, 2020, provisional application No. 63/015,690, filed on Apr. 27, 2020, provisional application No. 63/001,333, filed on Mar. 29, 2020.

(51) Int. Cl.
*A61N 5/00* (2006.01)
*A61M 1/36* (2006.01)
*A61N 5/06* (2006.01)
*A61N 5/067* (2006.01)

(52) U.S. Cl.
CPC ......... *A61M 1/3683* (2014.02); *A61N 5/0624* (2013.01); *A61N 5/067* (2021.08); *A61M 2202/206* (2013.01); *A61N 2005/063* (2013.01)

(58) Field of Classification Search
None
See application file for complete search history.

(56) References Cited

U.S. PATENT DOCUMENTS

| | | | |
|---|---|---|---|
| 7,753,869 B2 * | 7/2010 | Davidner | A61M 1/3468 210/645 |
| 8,808,977 B2 * | 8/2014 | Wu | A61L 2/0011 604/20 |
| 10,543,123 B2 * | 1/2020 | Neev | A61F 9/00827 |
| 10,588,694 B1 * | 3/2020 | Neev | A61B 18/203 |
| 11,813,368 B2 * | 11/2023 | Rabiner | A61L 2/0052 |
| 2010/0136646 A1 * | 6/2010 | Tsen | C12N 13/00 435/173.1 |
| 2013/0131423 A1 * | 5/2013 | Wang | A61M 1/3621 604/522 |
| 2019/0209376 A1 * | 7/2019 | Neev | A61F 9/00827 |
| 2023/0077399 A1 * | 3/2023 | Rabiner | A61L 2/084 |

FOREIGN PATENT DOCUMENTS

KR    20200015323 A  * 10/2018 ............ C21M 37/00

* cited by examiner

*Primary Examiner* — Shirley X Jian
(74) *Attorney, Agent, or Firm* — Daniel J Swirsky; Richard B Cates

(57) ABSTRACT

A method for damaging viruses in a human tissue comprised generating a series of ultra-short pulse laser (USPL) pulses by a USPL generator, radiating the USPL pulses by a USPL applicator and exposing the human tissue to a defined number of generated USPL pulses wherein an energy absorbing enhancing substance is disposed between the human tissue and the USPL applicator.

15 Claims, 4 Drawing Sheets

SYSTEM AND METHOD FOR DAMAGING VIRUSES

CROSS REFERENCE TO RELATED APPLICATIONS

This application claiming the benefit of U.S. Provisional Patent Application No. 63/001,333, filed Mar. 29, 2020; and U.S. Provisional Patent Application No. 63/015,690, filed Apr. 27, 2020; and U.S. Provisional Patent Application No. 63/075,125, filed Sep. 5, 2020, all of which are hereby incorporated by reference.

BACKGROUND OF THE INVENTION

The most common treatment of viral infections, such as human immunodeficiency virus (HIV), hepatitis, and influenza, Ebola, herpes, and HPV, among many others, is done typically by antiviral drugs are of very limited efficacy. Beyond anti-viral drugs there are substantially no effective approaches to treating virally infected people.

For instance, according to data published by the World Health Organization (WHO), hepatitis B caused around 887,000 deaths in 2015. Moreover, it was estimated that around 257 million patients were living with hepatitis B virus (HBV) infection in 2015. This is expected to drive the demand for efficient treatment solutions such as antiviral drug. Not only the rate of infection and rates of mortality and morbidity are unknown, but psychological uncertainty and fear make rational analysis of what people are willing to pay becomes more difficult.

The coronavirus attacks the respiratory pathways, including the upper respiratory tract, the trachea, peripheral areas of the lungs and other central airways. When the virus reaches the lungs its mucous membranes become inflamed and pneumonia can occur. Reducing the viral load in the mucous membranes of the lungs reduces the risk of pneumonia and ARDS (Acute Respiratory Distress Syndrome), which can require the use of oxygen therapy, with or without mechanical ventilation, and lead to increased morbidity and mortality rates.

Currently viral infections are treated using antiviral drugs, which have a limited availability and efficacy. Patients with severe difficulty of breathing are treated using oxygen therapy which improves the ability of the inflicted lungs to absorb oxygen. Unfortunately, these treatment modalities are limited by the number of mechanical ventilation systems, invasive and non-invasive. More importantly, if the rise viral count is not arrested and, preferably, reversed, the infection continues to spread damaging additional region of the lungs and body.

There is a need for a system and methods of treating viral infections, whether in the blood or in body tissues and organs which provide high efficacy alongside very little undesired or dangerous impact on the patient's medical condition.

SUMMARY OF THE INVENTION

A method for damaging viruses in a human tissue is presented the method comprising generating a series of ultra-short pulse laser (USPL) pulses by a USPL generator, radiating the USPL pulses by a USPL applicator and exposing the human tissue to a defined number of generated USPL pulses wherein an energy absorbing enhancing substance is disposed between the human tissue and the USPL applicator.

In some embodiments the human tissue is one or more from organelle, flesh tissue, bone, lymphatic tissue, circulatory body fluid and blood.

In some embodiments the USPL pulses duration is between 3 femtosecond and 100 picosecond.

In some embodiments the USPL pulse duration is between 3 femtosecond and 10 picosecond.

In some embodiments a pulsed electromagnetic energy is focused in one or more spatial locations into a human tissue such as one or more from organelle, flesh tissue, bone, lymphatic tissue, circulatory body fluid and blood and generate a shockwave in one or more spatial locations within a human tissue.

In some embodiments the radiation of the USPL pulses by a USPL applicator is configured to excite opto-mechanical shockwave in the energy absorbing enhancing substance.

In further embodiment of the present invention the shockwave energy absorbed by virus particles is sufficient to inactivate at least some of the virus particles, while the energy absorbed by the cells leave the cells unharmed.

In some embodiments the amount of energy provided by the radiated USPL pulses is between 1 mJ and 10 mJ.

In some embodiment the amount of energy provided by the radiated USPL pulses is between 1 nJ and 10 mJ.

In some embodiment the amount of energy provided by the each of the radiated USPL pulses is between 1 microjoule and 30 mJ.

In some embodiments the human tissue is human blood.

In some embodiments the human blood is mixed with an energy absorbing enhancing substance prior to the radiation by USPL pulses. In some additional embodiments the energy absorbing enhancing substance is removed from the human blood after the radiation by USPL pulses.

In some embodiments the radiation of the human organ is done using optical guide.

A system damaging viruses in a human tissue is presented comprising an ultra-short pulse laser (USPL) generator configured to generate laser pulses with pulse duration between 3 femtosecond and 100 picosecond and radiation duration of the pulses between 1 second and 10 hours.

In some embodiments the system further comprising a controller configured to control the duration of the pulses and the duration of the radiation.

In some embodiments the controller is configured to control the optical energy provided by the USPL generator.

In some embodiments the system further comprising power supply unit.

In some embodiments the radiation chamber is configured to impose laminar flow of the blood flowing through it.

In some embodiments the system further comprising an optical guide configured to pass the pulses generated by the USPL generator from a proximal end of the optical guide to a distal end of the optical guide.

In some embodiments the optical guide is insertable through a catheter.

In some embodiments further the system comprising a member for redirecting said pulse energy onto the viruses one or more times.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
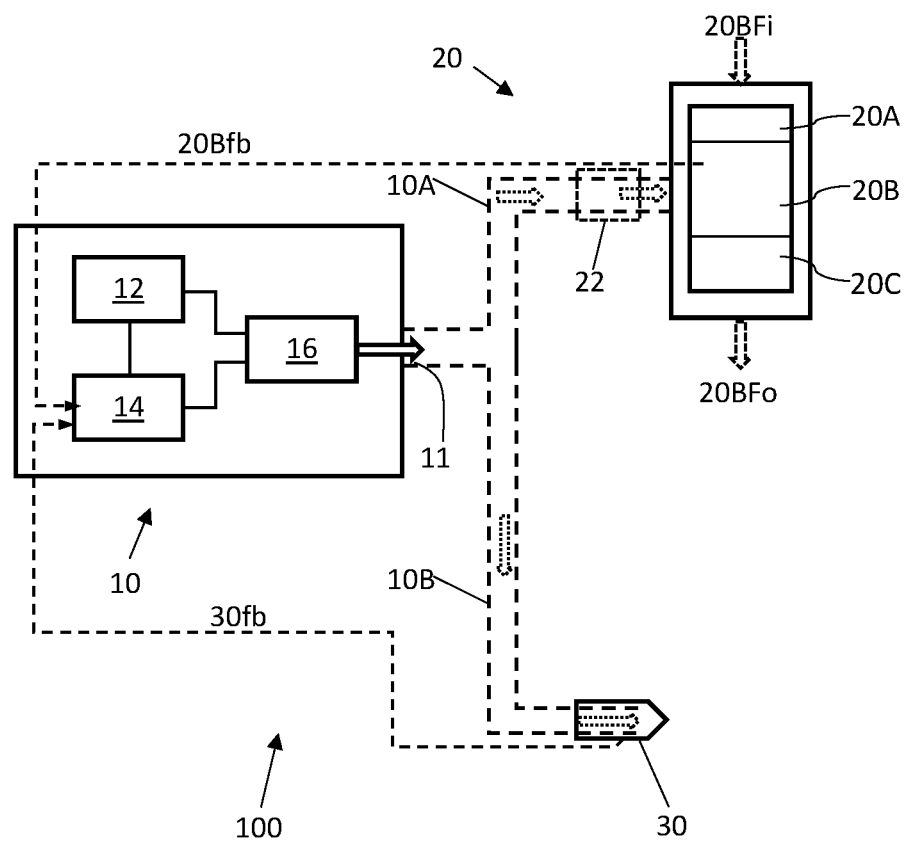
FIG. 1 is a schematic block diagram of a system for damaging viruses, according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

A unique ability is presented, according to embodiments of the invention, to non-chemically, non-systemic (i.e. without the need for introducing chemical compounds to the entire human body) delivery of damaging impact which may specifically be targeted to the viruses. Treatment according to embodiments of the invention may significantly impact the body viral load and thus allow the patient's precious time to recover, build up its impunity, and possibly altogether eliminated the threat. Impacting the viral load in patients organs provides relief and time and slow the rate of illness progression, thus reducing the number of the required ventilators and shortening the duration of use by shortening the time to recovery, which can significantly affect the ability of hospitals to handle a mass infection and a large number of simultaneous patients.

A device according to embodiments of the invention can be used to treat respiratory viral infections in general and the coronavirus specifically. The device may mainly be used to treat patients with severe symptoms or in critical conditions. The estimated share of these patients in the laboratory-confirmed coronavirus patient population is approximately 5%. Therefore, assuming 50% of the population is affected eventually, the device can be used on 450,000 patients in Israel and millions of patients world-wide. In addition, the device can be used for other viral respiratory infections and can therefore reduce morbidity and mortality associated with other common viruses, such as the common flu, significantly increasing the potential market size. In some embodiments a system and treatment methods of the invention may provide an easy, non-invasive, outpatient treatment modality that can be applied rapidly and widely, outside the hospital settings, in the field and at a variety of outposts within the afflicted communities, treating patients with even early symptoms to prevent progress and spread of the disease.

Prior art trials of using Impulse Stimulated Raman Scattering (ISRS) showed low efficacy and required very long treatment cycles.

In embodiments of the present invention a system based on an ultrashort pulse laser (USPL) is configured to provide femtosecond pulses in order to deliver targeted energy treatment to infected blood or tissues and, possibly, early treating of containment of viral infections. As is used herein the term 'tissue' may refer to skin tissue, muscle, blood, bone, lymphatic fluid, hard dental tissue, etc.

USPL lasers, operative in the pulse duration regime of about 10 picoseconds or shorter, are characterized by the fact that only the electrons of the material lattice are able to respond to such short pulse. The atomic nucleus does not respond to the energy of the pulse by the time the pulse is over. The electrons do respond and due to the short time durations, multiple photon combine their energy to give the electrons ionization kinetic energy and they break off the matter. This demonstrates a consistent way (not statistical) ensuring that the seed electrons are always generated, and plasma is initiated and, if enough energy per pulse, also shockwave in the medium is created. As is known in the art pulses duration of nanoseconds, picoseconds, microseconds and even milliseconds and longer pulses, if energetic enough, or if encountering high enough absorbing substances, may also generate seed electrons and plasmas and micro shockwaves, yet the energy enabling this is respectively much higher. Further, the energy required for generating effective micro shockwaves usable for damaging viruses may be lowered by using energy absorbing substance with higher absorbing coefficient, such as carbon-based inks.

The interaction of USP Lasers with materials can be summarized in the following way. Electrons oscillating in the laser field gain energy as a result of phonon scattering (Joule heating). When the electron energy exceeds the band gap, new electrons are ionized generating an electron avalanche. Experimentally, it has been shown that the damage threshold to dielectrics decreases with laser pulse duration, approximately according to the dependence. This result is a consequence of the thermal origin of the energy coupling process. At the same time, the extent of collateral damage also decreases with the pulse duration. For ultrashort pulses (pulses shorter than 10 ps), the physics of the interaction changes. Here, the direct production of free electrons via multiphoton absorption (MPA) is crucially important. Even when total number of electrons produced by MPA is small they provide the initial, seed electron for avalanche. As a result, the ablation threshold for USPL is independent of material defects and insensitive to linear absorption. Experimentally, it is manifested as a deviation from the dependence and through a modification to the damage morphology. Specifically, ultrashort pulse absorption is characterized by the following:
1) Following seed electron generation via multiphoton ionization, avalanche process induced by the electromagnetic field continues to generate free electron in an exponential growth. Consequently, laser energy deposition increases exponentially as well.
2) The laser intensity is so high that MPA plays a key role. Generated via multiphoton absorption, free electrons absorb the energy from the laser light starting an ionization avalanche. Even transparent material becomes strongly absorbent, independent of the linear absorption characteristics.
3) When the density of free electrons in the plasma a exceeds critical density the plasma becomes highly reflective to incoming radiation.

At these higher electron densities, strong absorption of light takes place only in a thin layer whose thickness is inversely proportional to the square root of the plasma electron density. Energy is thus unable to penetrate into the material. As a result of this process, subsequent absorbed energy is deposited in this layer. The higher the electron densities, strong absorption of light takes place only in a thin layer whose thickness is inversely proportional to the square root of the plasma electron density, $n^{1/2}$. Energy is thus unable to penetrate into the material. In these ablative interactions of ultrashort pulses with matter, the estimated thickness of the material removed per pulse is given by $$a \sim Q/5Ee$$

where Q is the incoming laser pulse energy per unit area and Ee is the Evaporation Energy per unit volume. 5 indicates that beyond bond breaking the ejecta must be accelerated up to velocities and some of the absorbed energy will be used for it.

It is customary to define the threshold pulse energy as an energy sufficient to produce a conduction electron density equal the critical density. At this point, deposited energy is high enough to break material bonds and to evaporate tissue. When electron density exceeds, radiation can no longer penetrate into the material, and it is partly reflected back and partly absorbed in a thin surface layer. When all electrons are ionized in the surface layer, the optical depth of penetration does not decrease any further and subsequent incoming energy results in increased free electron energy in this layer while reflectivity continues to increase as well.

As was discussed above, the laser energy is deposited in a very thin layer of material and, consequently, deposited energy density is much larger than that of binding energy. After pulse termination, energy from the electrons is transferred to ions in the material lattice and material ejection takes place. The typical time scale for this latter process is nanoseconds a much longer time than the deposition time scale. Such a situation is typical for the problem of "impact loading". Because of its high deposited energy density, the material can be considered as an ideal gas and we expect that the time evolution will be self-similar. The shock propagating into the material heats and evaporates material below the deposition zone.

Shockwaves are propagating mechanical disturbances that move faster than the local speed of sound in the medium. Like an ordinary wave, a shockwave carries energy and can propagate through a medium but are characterized by an abrupt, nearly discontinuous, change in pressure, temperature, and density of the medium. Importantly, the arrival of the energy associated with a shockwave at the discontinuous boundary of an object positioned within the medium carrying the shockwave, loads up the object with large amount of energy in a very short time period. If the mechanical properties of the object are such that it cannot release the deposited energy in a non-distractive manner, the deposited shockwave energy may cause irreversible changes to the object structure and will irreversibly damage it. If the object in the path of the shockwave is a virus, and/or the virus shell (the Capsid) such destructive interaction may constitute a very useful way to damage and/or inactivate the virions.

The ability of an object confronted by propagating shockwave to release, or dissipate the energy brought upon it by the shockwave is a function of the structure of the object and also the size (or mass) of the object. The higher the size of the object the higher its ability to dissipate an energy brought by a propagating shockwave. The amount of damage depends on the intercepting object mechanical properties (i.e. its ability to release the rapid energy loading in a reversible, elastic manner) and on the power density of the shock front. As is known in the art, virus shell size is much smaller than human cells and by way of example, the amount of power per unit area (energy per time per impact area) required for deactivation of the M13 virus, the TMV, the HPV virus, and the HIV virus were (in $GW/cm^2$) is 0.06, 0.85, 1.0, and 1.1. Respectively. By contrast, damage to human blood cells, human Jurkat T cells, and mouse dendritic cells are 15, 22, and 12 $GW/cm^2$, respectively.

In accordance with some embodiments of the invention virus cells in human tissue may be targeted by providing specific energy of no more than, for example, 1.1 $GW/cm^2$, thereby sparing a safety gap of at least one magnitude of order of the energy provided to the human tissue while ensuring high damaging/deactivation of viruses in the human tissue, as explained below. It should be noted that shockwaves can be created by a variety of mechanisms including electric discharge, supersonic objects, and explosive material (e.g. TNT) ignition.

Femtosecond laser have been proven to induce shock front damage to the virion capsid, however, the energy of a shockwave that is capable of damaging a virion capsid is unable to damage a membrane of a human cell, due to the human cell's ability to dissipate and attenuate the energy of the shockwave front. According to embodiments of the invention, in order to successfully target viruses within a human tissue and damage or inactivate them without damaging human cells the limited level of specific energy (energy per area unit) required for damaging the virion capsid can propagate via medium with high energy absorption factor, which turns to act as shockwave propagation medium, thereby capable of transferring the shockwave energy to viruses found within the medium with high energy absorption factor. High absorption substance (HAS), energy absorption enhancing substance (EAES) such as, by nonlimiting example, gold nano particles, gold nanorods, carbon particles, nanodroplets of ink, micro-size droplets of high absorbing substances etc.

In experiments for forming High absorption substance (HAS), Nanotetrapods (NTR) were used with concentrations ranging from 10 E9 ($10^9$) NTR per microliter to 10 E13 ($10^{13}$) per microleter and in particular concentrations of from 10 E10 ($10^{10}$) per microleter to 10 E 12 ($10^{12}$) per microleter and most often 10 E10 ($10^{10}$) NTR per microliters.

In the case of ink microdropletes or ink nanodroplets the concentration can range from, for example 1 microliter (uL) of ink per mL of treated fluid to 250 uL of ink per mL of blood or mL of water or mL of other liquids. Or, more preferably from about 10 uL of ink per mL of liquid blood or liquid host to 100 uL, and yet more preferably from 20 uL of liquid ink to 100 uL of liquid ink within 1 mL of liquid host media (e.g., blood). And most preferably from 10 uL of liquid ink to 1 mL of host medium to 50 ul of liquid ink per 1 mL of host blood or host medium.

It would be apparent to those skilled in the art that according to embodiments of the invention described herein, any required shock wave with sufficiently concentrated pulse energy may be created, in accordance with the nature and amount of treated tissue, and any HAS chemical and/or substances may be removed after the virus damaging process by doing away with all absorption enhancing substance.

Generation of ultrashort pulses from a range as low as sub-picosecond time durations, allows creating shockwave with per-pulse energies of millijoule (mJ), micro-joule (uJ), and even sub-micro-joule energy packages. Such shockwave generation mechanisms, for example, are used in ophthalmic surgery utilizing femtosecond pulse lasers to create thousands of micro-bubbles that are used to cut the cornea, the crystalline lens in cataract surgery, and other surgical targets within the eyes. For example, the femtosecond lasers used in eyes surgery use pulse energy in the micro-joule range to generate such microplasmas and micro shockwaves. The ability to condense minute energy both in time and in space allows utilizing USP lasers to create shockwave within the three-dimensional space of the virus carrying medium. The fact that only small amounts of energy are needed mean that the targeting can be localized and spare unintended regions. An ultrashort pulse from a laser can be calibrated to release small enough energy to damage virions in the human tissue such as blood, but not damage the much larger cells or the cellular organelle of a human which are protected by the cell membrane.

Embodiments of the present invention present two main modalities of treatment usable for damaging viruses in human. The first modality is an ex-vivo treatment adapted to treat body fluids ex-vivo. The treatable body fluids may comprise blood and lymphatic fluid. The second modality is an in-vivo treatment which comprises placing a distal tip of a shockwave generator inside a body next or close to or to the vicinity of a tissue or organ with viruses to enable providing electromagnetic (EM)-mechanic shockwaves to the viral tissue or organ. In some embodiments the EM energy may be in the optic wavelength range and the generation of shockwave may be done by a USPL generator.

Reference is made now to FIG. 1, which is a schematic block diagram of system 100 for damaging viruses, according to embodiments of the present invention. System 100 may comprise an ultra-short pulse laser (USPL) generator assembly 10 that may be connected to an ex-vivo body fluid virus damaging applicator 20 via optical guide 10A or to an in-vivo virus damaging applicator 30 via optical guide 10B. USPL assembly 10 may comprise USP laser 16 that may be any known ultra-short pulse laser generator adapted to provide laser pulses of duration in the range from 10,000 femtosecond to 3 femtosecond, at a pulse rate between 1 Hz and 1 GHz, and more preferably from 100 Hz to 100 MHz, and more preferably from 500 Hz (0.5 KHz) to 50 MHz, and more preferably yet, from 0.5 KHz to 500 KHz, and more preferably yet from 1 KHz to 350 KHz, and most preferably from 10 KHz to 250 KH, providing radiation for a total time duration of between 1 second and 10 hours, and more preferably between 5 seconds and 3 hours, and more preferably yet, for a time duration of between 5 seconds and 10 minutes. Alternatively, or additionally, such total exposure time may be short enough to be repeated in finite intervals, repeatedly, several times during a total patient treatment time of, for example two to six hours. For example, a laser exposure time of 10 seconds repeated 100 times in an hour. Or a laser exposure time of fifteen seconds repeated 200 to 400 times in a total patient treatment time of 4 hours.

Additionally, the per pulse energy of the laser energy source at the target treated patient may range from ten nano-Joules per pulse to 10 Joules per pulse and more preferably from half a micro-Joule per pulse to 5 Joules per pulse and more preferably from 5 micro joule to 10 millijoule per pulse.

In some embodiments USPL generator assembly 10 may comprise power supply 12 adapted to provide the required power to ultra-short pulse laser 16, and to USPL control unit 14. Control unit 14 may be configured to control the work parameters of USPL generator assembly 10, for example the pulses duration, the pulses repetition policy (e.g. pulses gaps and pulses count) the pulse energy and the overall energy produced and provided during the virus damaging cycle. In some embodiments control unit 14 may receive feedback signal, such as signal 20Bfb indicative of the USPL absorption rate during ex-vivo virus damaging process, or signal 30*fb* indicative of the USPL absorption rate during in-vivo virus damaging process. Such feedback signal, when provided, may be considered in order to accurately tune the virus damaging parameters. Further elaboration of in-vivo applicator 30 is found below in the detailed description of FIGS. 4A and 4B.

Ex-vivo fluid virus damaging applicator 20 may be configured for receiving body fluid (e.g. patient's blood) through applicator's fluid input port 20BFi, to pass the received fluid through high absorption substance enhancement section 20A, where such substance (e.g. gold nanorods, gold Nanotetrapods, magnetic nanorods, magnetic nanoparticles, carbon nanoparticles, Nanotetrapods, nano or micro ink droplets, etc.) may be added to the fluid in order to magnify the effect of the shockwave, then the fluid may pass to USPL radiation section 20B to be treated, and after the virus damaging treatment the fluid may pass through additives removal section 20C before the treated fluid flows out of the treatment process through output port 20BFo. Means and methods for mixing the fluid with absorption enhancing substance before the treatment and means and methods for removal of the absorption enhancing substance from the fluid after the treatment may be done in any known manner, in connection with the absorption enhancing substance use. In order to enhance the impact of the radiated USPL pulses section 20B of the fluid virus damaging applicator 20 may be configured to cause laminar flow of the fluid in a plane that is substantially perpendicular to the direction of radiation of the USPL energy dissipation, for example based on well-known fluidics engineering means and methods. Proper selection of the USPL radiation parameters may enable successful radiating of 5 litters of fluid during a reasonable clinical treatment time using no more than 10 mJ per pulse energy. It would be apparent to those skilled in the art that the process of damaging viruses that was exemplified above may be performed during, for example, dialysis process without delaying the dialysis process.

Treatment for damaging viruses in human tissue ex-vivo (also called herein Viralysis) may be done by a system according to the present invention having, for example, a sub-picosecond USPL system of 300 W, operating at 300 KHz with radiation energy of approximately 1 mJ per pulse. Energy of 1 mJ per pulse was used to treat 1 CM3 of virions with 10 sec radiation time at 1 KHz pulses repetition rate, i.e. about 10 E4 ($10^4$) pulses to treat 1 cm3. A more power (high average power) proposed by the present invention is using a fiber USPL system of 300 KHz, which may enable treatment in 1/300 less time to treat 1 cm3 (i.e. 1 ml of blood), i.e. 10 sec/300=0.03 sec to treat 1 cm3 or 1 ml of blood.

Assuming an average blood volume of about 5 Liter to be treated (e.g. if the anti-virus treatment is performed during dialysis treatment cycle) we get:

5000 ml×0.03 sec/ml=150 sec i.e. a Treatment time of ~=2.5 minutes for the entire 5 liter of infected patient blood. Note however, that this is a theoretical treatment time based on the USPL capability only. IN practice, the practical medical limitation of extracting and re-introducing the blood into the patient need to be considered, assumingly slowing dramatically the virus damaging treatment. These considerations are, of course, physiological in nature and depend on many factors including the patient health. That actual treatment time will likely be more in the range of the time it takes to treat dialysis patients, e.g. from 3 hours to as long as six hours.

Ex-vivo fluid virus damaging applicator 20 may further comprise optical stack 22, adapted to manipulate the USPL pulses received from USPL assembly 10 in order to provide substantially even spread of energy to the radiated fluid. Optical stack may comprise one or more mirrors, one or more lenses and/or one or more optical splitters.

Ex-vivo treatment according to embodiments of the present invention may be provided for treating virus particles ex-vivo within the blood (or other hosting liquid and/or fluids), by extracting blood out of a patient body and pre-process treating the blood in order to enhance its ability to absorb USPL shockwave energy. Enhancing the ability to absorb USPL shockwave energy may be achieved by adding into the treated fluid (e.g. the patient blood) an electromagnetic resonant (EMR) and/or other energy absorption enhancing substance that can enhance the energy absorption and allow more efficient generation of shock wave. The Energy Absorption Enhancing Substance (EAES) may enhance the generation of shock wave and/or other damaging energy forms adapted to damage the virus particles. After the body fluid was treated ex-vivo the HAS or EAES can be removed from the blood or other body fluid (for example, by magnetically separating metal nanorods, metal nanoparticles, magnetic nanoparticles or nanorods, or by filtering out high absorbing substance (HAS) or ink micro-droplets. Etc.) The anti-virus treated blood may subsequently be re-introduced into the patient blood circulation.

In-vivo virus damaging process may be done using in-vivo virus damaging applicator 30. Applicator 30 may be connected via optical guide 10B to the USPL pulses output 11 of USPL generator 16. Applicator 30 and optical guide 10B may be adapted, in size, form and materials, to be inserted into a viral organ, tissue of body lumen using, for example laparoscopic techniques (e.g. —inserted via a catheter) until applicator 30 is positioned close to or within the body lumen or tissue that needs to be treated. Advance understanding where in a patient's body there is viral zone that should be treated may be done using any suitable known method, such as by CT or MRI imaging. Then, a professional may decide what may be the recommended path for inserting applicator 30 and optical guide 10B so that applicator 30 gets as close as needed to the viral zone, e.g. by inserting a catheter via blood vessel and inserting applicator 30 and its optical guide 10B through the catheter. Further elaboration of in-vivo applicator 30 is found below in the detailed description of FIGS. 4A and 4B, herein below.

Figure 2:
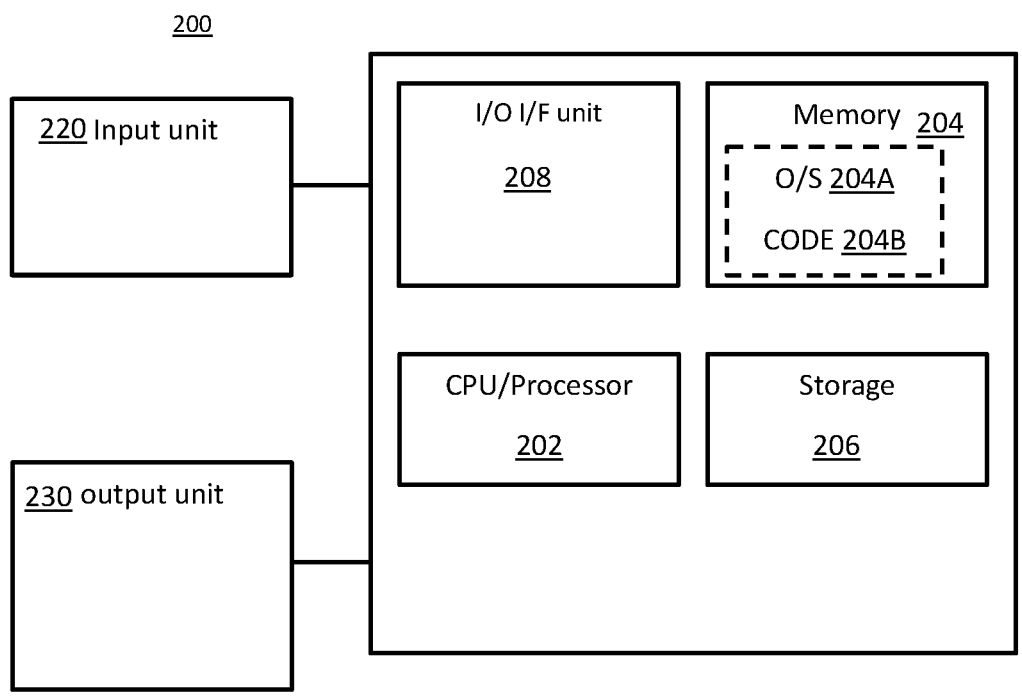
FIG. 2 is a schematic block diagram of a computing system usable with the system of FIG. 1, according to embodiments of the invention.

Reference is made now to FIG. 2, which is a schematic block diagram of computing system 200, according to embodiments of the invention. Control unit 200 may be similar or identical to control unit 14 of FIG. 1. Control unit 200 may comprise processor 202, memory unit 204, storage device 206 and input/output (I/O) interface (I/F) unit 208. Computing system 200 may further comprise input unit 220 and output unit 230.

Processor 202 may be, for example, a central processing unit processor (CPU), a chip or any suitable computing or computational device. Processor 202 (or one or more processors, possibly across multiple units or devices) may be configured to carry out methods described herein, and/or to execute or act as the various modules, units, etc. More than one control unit 200 may be included in, and one or more control units 200 may act as the components of a system according to embodiments of the invention.

Memory unit 204 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 104 may be or may include a plurality of possibly different memory units. Memory unit 104 may be a computer or processor non-transitory readable medium, or a computer non-transitory storage medium, e.g., a RAM.

Storage unit 206 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) storage device or other suitable removable and/or fixed storage unit. Content may be stored in storage unit 206 and may be loaded from storage unit 206 into memory unit 204 where it may be processed by processor 202. In some embodiments, some of the components shown in FIG. 2 may be omitted. For example, memory unit 204 may be a non-volatile memory having the storage capacity of storage unit 206. Accordingly, although shown as a separate component, storage unit 206 may be embedded or included in memory unit 104.

Control unit 200 may further comprise I/O interface (I/F) unit 208, which is configured to enable communication and connectivity of input unit 220 and output unit 230 to computing control unit 200. Processor 202, memory unit 204, storage unit 206 and I/O interface unit 208 may be in operational connection with each other.

Input unit 220 may be or may include any suitable input devices, components or systems, e.g., a keyboard or keypad, a mouse, a touch screen, digital or analogue feedback signal(s) and the like. Output unit 230 may include one or more (possibly detachable) displays or monitors, speakers and/or any other suitable output devices. Any applicable input/output (I/O) devices may be connected to control unit 200 as shown by blocks 220 and 230. For example, a wired or wireless network interface card (NIC), a universal serial bus (USB) device or external hard drive may be included in input devices 220 and/or output devices 230. It will be recognized that any suitable number of input devices 220 and output device 230 may be operatively connected to computing system 200 as shown by blocks 220 and 230.

control unit 200 may comprise operating system 204A that may be stored or loaded into memory unit 204. Operating system 204A may be or may include any code segment (e.g., one similar to executable code 204B described herein) designed and/or configured to perform tasks involving coordination, scheduling, arbitration, supervising, controlling or otherwise managing operation of computing system 200, for example, scheduling execution of software programs or tasks or enabling software programs or other modules or units to communicate. Operating system 204A may be a commercial operating system. It will be noted that an operating system 204A may be an optional component, e.g., in some embodiments, a system may include a computing device that does not require or include an operating system 204A. Computing system may comprise executable code 204B which may be any executable code, e.g., an application, a program, a process, task or script. Executable code 204B may be executed by processor 202, possibly under control of operating system 204A. Although, for the sake of clarity, a single item of executable code 204B is shown in FIG. 1B, system according to some embodiments of the invention may include a plurality of executable code segments similar to executable code 204B that may be loaded into memory unit 204 and cause processor 202, when executed, to carry out methods described herein.

Figure 3:
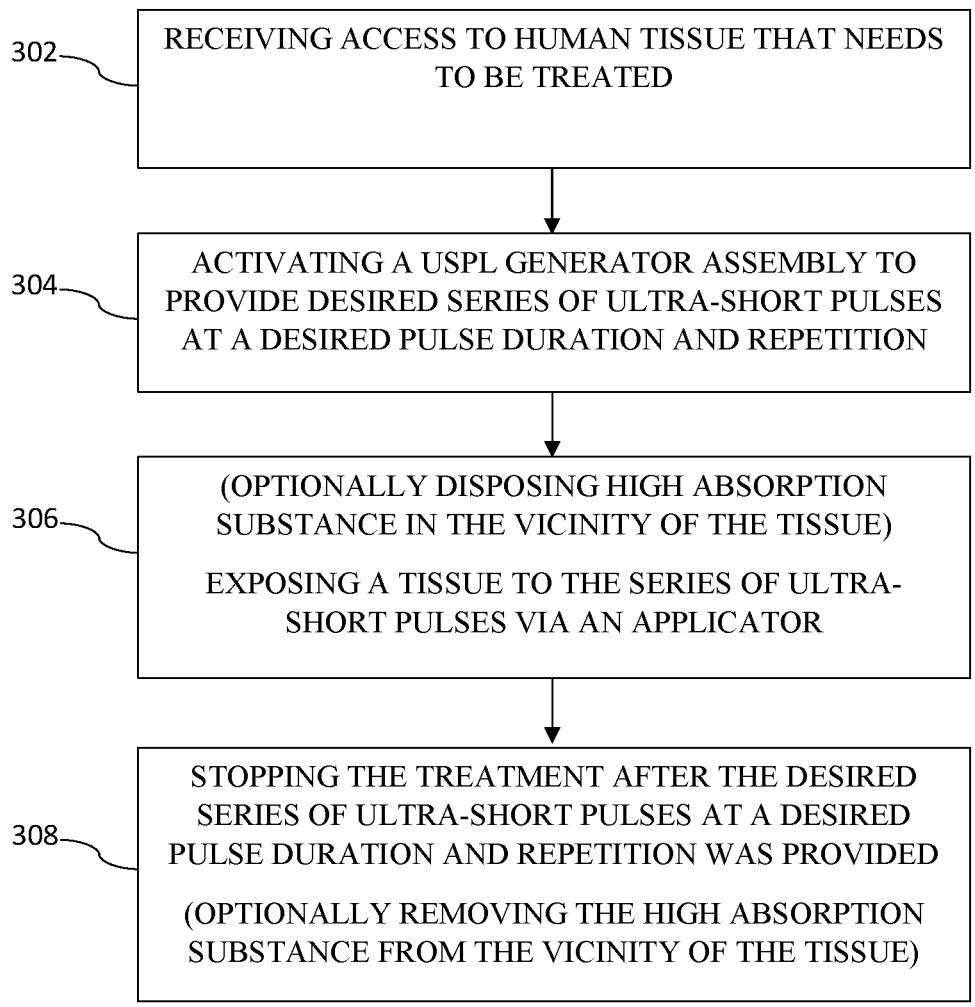
FIG. 3 is a schematic flow diagram depicting a method for damaging viruses in a human tissue, according to embodiments of the present invention.

Reference is made now to FIG. 3, which is a schematic flow diagram depicting a method for damaging viruses in a human tissue, according to embodiments of the present invention. First an access to human tissue that needs to be treated for damaging of viruses is received (step 302). A USPL generator assembly is activated to provide a desired series of ultra-short pulses as a desired duration and repetition scheme (step 304). In one embodiment the medium between the applicator of the USPL generator assembly and the tissue may be provided with high absorption substance to enhance the energetic effect of the USPL pulses and then the tissue may be exposed to the series of ultra-short pulses (step 306). After the series of ultra-short pulses finishes the operation of the USPL generator assembly is stopped and, if high absorption substance was added to the tissue it may now be removed from the tissue (step 308).

Figure 4A:
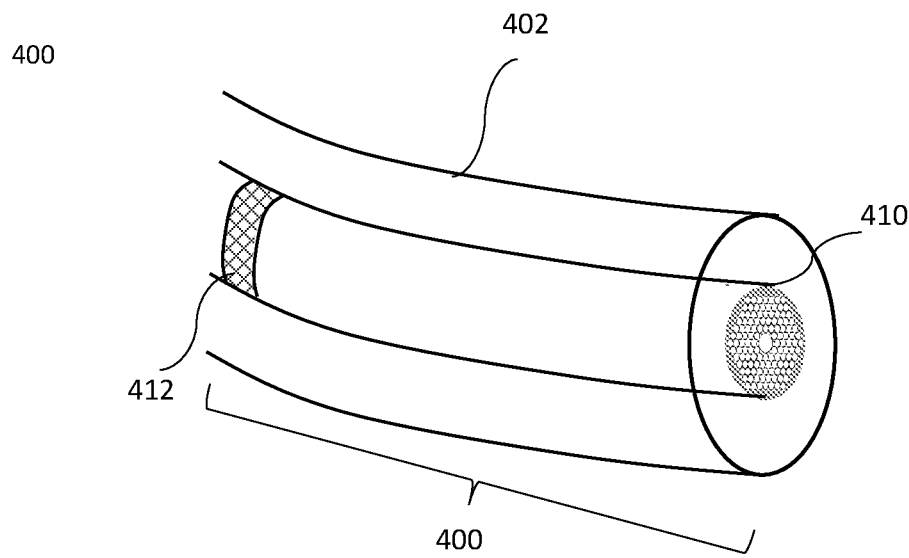
FIG. 4A is a partial schematic illustration of an in-vivo applicator according to embodiments of the present invention.
Figure 4B:
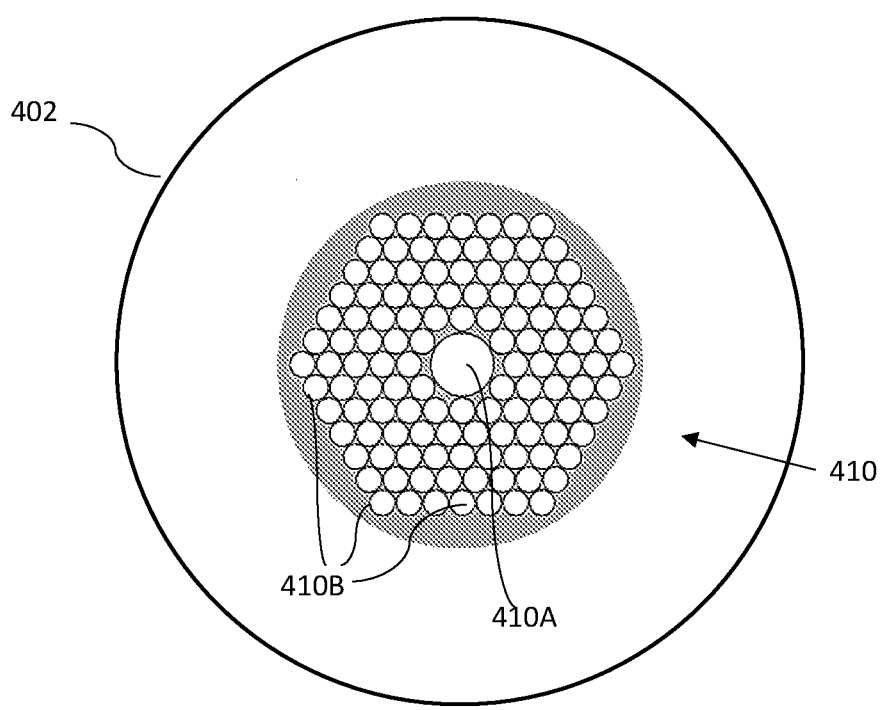
FIG. 4B is a schematic enlarged illustration of the tip of the applicator of FIG. 4A, according to embodiments of the present invention.

Reference is made now to FIG. 4A, which is a partial schematic illustration of an in-vivo applicator 400 and to FIG. 4B, which is a schematic enlarged illustration of the tip of applicator 400, according to embodiments of the present invention. An opto guide such as opto guide 10B of FIG. 1, for providing in-vivo treatment for damaging viruses may be inserted into a body lumen via, for example, a blood vessel using a catheter as is known in the art. FIG. 4A schematically presents the distal end of an in-vivo applicator 400 (similar to applicator 30 of FIG. 1) within blood vessel 402. Note that the guiding catheter is now shown for the sake of improved clarity of the drawing. The opto-guide may be of the hollow core-photonic crystal fiber (HCPCF) type, having a central core and multiple hollow perforations around it. FIG. 4B demonstrates a typical cross section of a HCPCF opto guide 410 having a central core 410A and multiple hollow micro tubes 410B around it. Optical energy may be guided within central core 410A. Some known technique were developed for forcing nanoparticles into the HCPCF and/or microstructures fibers. As explained above with regard to ex-vivo treatment of viruses in fluids, presence of absorption enhancing nanoparticles improves the effect of the USPL in damaging viruses. According to embodiments of the present invention such nanoparticles may be forced into the structure of HCPCF opto guide 410 such that when USPL energy is provided to applicator 400 for example via central core 410A and body fluid (e.g., blood) flows between applicator 400 and the blood vessel wall, the energetic effect of the USPL pulses is enhanced due to the presence of the nanoparticles.

In some embodiments blood may also be allowed to flow though hollow micro tubes 410B thereby this flow may better be effected by the USPL pulses provided via central core 410A. in order to enable flow of blood via hollow micro tubes 410B release perforation section 412 (FIG. 4A) may be done on the external envelope of applicator 400, thereby allowing flow of blood though hollow micro tubes 410B from the distal tip 410 through hollow micro tubes 410B and out of applicator 400 via perforation section 412.

Femtosecond pulses of wavelengths between 1100 nm-2200 nm are scattered much less strongly than pulses with a wavelength around 775 nm. With the application of tissue optical clearing device according to embodiments of the invention, water and blood concentration in the tissue is reduced so that the absorption of light with wavelengths in the 1100-2200 nm is reduced. Based on these experiments femtosecond pulses comprised of wavelengths in the 1100-2200 nm spectral range can penetrate deeper and provide superior subsurface cavities compared to 800 nm femtosecond pulses. In intracorporeal and intravenous irradiation nano or micro absorbers embedded in the floor of blood treatment chamber may be employed (see FIG. 1) or in a hollow waveguide or a photonic bandgap fiber, where the blood flow through a hollow core fiber media that incorporate nanostructures and/or microstructures embedded in the HC fibers walls to initiate absorption, seeding of free electron, and subsequent microplasmas and shockwave driven by the energy of pulses passing by. Gold or metal Nanoparticles, Nanorods, or micro droplets/inks, etc. may provide localization of the shock-fronts to the vicinity of the virus particles instead of inducing a larger shock-front throughout the media (i.e. through a much larger volume of the treated blood). The actual physical dimension of the HCPCF optoguide can vary depending, for example, on the targeted blood vessels and organs. Yet even for the smallest blood vessels, HC fibers as small as 100 um and less will allow up to intercede and introduce energetic ultrashort pulses to the smallest blood vessels, air tubes, and air passage in the body and within the lungs, heart, and other organs.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for damaging viruses in a human tissue the method comprising:
   generating a series of ultra-short pulse laser (USPL) pulses by a USPL generator, the USPL pulses having at least one of a pulse duration of between 3 femtosecond and 100 picosecond, and a duration of application of between 1 second and 10 hours; and transmitting a predefined number of the USPL pulses towards the human tissue, the human tissue comprising an energy absorbance enhancing substance, wherein the USPL pulses are configured to excite opto-mechanical shockwaves in the energy absorbance enhancing substance, the opto-mechanical shockwaves having an energy sufficient to inactivate at least some viruses in the human tissue when absorbed by the viruses, but insufficient to harm cells of the human tissue when absorbed by the cells of the human tissue.

2. The method of claim 1 wherein the human tissue is one or more of organelle, flesh tissue, bone, lymphatic tissue, circulatory body fluid and blood.

3. The method of claim 2, wherein the human tissue is blood, and the blood is radiated by the USPL pulses ex-vivo.

4. The method of claim 3, wherein the blood is mixed with the energy absorbance enhancing substance prior to exposure to the USPL pulses.

5. The method of claim 3, wherein the energy absorbance enhancing substance is removed from the human blood after the exposure to the USPL pulses.

6. The method of claim 1, wherein the amount of energy provided by the USPL pulses is between 1 nJ and 10 mJ.

7. The method of claim 1 wherein the amount of energy provided by each of the USPL pulses is between 1 microjoule and 30 mJ.

8. The method of claim 1, wherein the transmission of the USPL pulses is performed using an optical guide.

9. The method of claim 8, wherein the optical guide is adapted to be brought close to the human tissue using a catheter.

10. A system for damaging viruses in a human tissue, comprising:

an ultra-short pulse laser (USPL) generator configured to generate USPL pulses which produce opto-mechanical shockwaves when impinging on an energy absorbance enhancing substance, the laser generator being adapted to generate USPL pulses having at least one of a pulse duration between 3 femtosecond and 100 picosecond, and a duration of the application of the USPL pulses to the human tissue of between 1 second and 10 hours; and an applicator adapted to transmit the USPL pulses from the generator to the human tissue, such that when the human tissue comprises the energy absorbance enhancing substance, the energy of the generated shockwaves absorbed by the human tissue is sufficient to inactivate at least some of the viruses, while the energy of the generated shockwaves absorbed by cells of the human tissue is insufficient to harm the cells.

11. The system of claim 10, where the human tissue is a flow of human blood, the system adapted to enable radiation of the human blood flowing through a radiation chamber, by the USPL pulses.

12. The system of claim 11, wherein the radiation chamber is configured to cause laminar flow of the blood flowing through it.

13. The system of claim 10 where the applicator comprises an optical guide.

14. The system of claim 13, wherein the optical guide is insertable through a catheter.

15. The system of claim 10 further comprising a member for directing the pulses towards regions containing viruses in the human tissue.

* * * * *